United States Patent [19]

Correia et al.

[11] 4,172,957

[45] Oct. 30, 1979

[54] PRODUCTION OF MONOCHLOROACETYL CHLORIDE AND MONOCHLOROACETIC ACID BY HYDRATION OF TRICHLOROETHYLENE

[75] Inventors: Yves Correia, Chateau Arnoux; Gérard Dumas, Saint-Auban, both of France

[73] Assignee: Rhone-Poulenc Industries, Paris, France

[21] Appl. No.: 923,792

[22] Filed: Jul. 12, 1978

[30] Foreign Application Priority Data

Mar. 22, 1978 [FR] France .................................. 78 08264

[51] Int. Cl.$^2$ ...................... C07C 51/00; C07C 53/16; C07C 53/20
[52] U.S. Cl. .................................... 562/602; 562/604; 260/544 Y
[58] Field of Search .................. 260/539 A, 544 Y; 562/602, 604

[56] References Cited

U.S. PATENT DOCUMENTS

| | | | |
|---|---|---|---|
| 1,304,108 | 5/1919 | Simon et al. | 260/544 Y X |
| 3,742,047 | 6/1973 | Prill | 260/544 Y X |
| 3,829,477 | 8/1974 | Strini | 260/544 Y X |

FOREIGN PATENT DOCUMENTS

| | | |
|---|---|---|
| 516367 | 12/1920 | France. |
| 2070427 | 8/1971 | France. |
| 86192 | 5/1919 | Switzerland. |

*Primary Examiner*—Gerald A. Schwartz
*Attorney, Agent, or Firm*—McDougall, Hersh & Scott

[57] ABSTRACT

Continuous process for the production of monochloroacetyl chloride accompanied, if the need should arise, by monochloroacetic acid, from trichloroethylene and/or 1,1,1,2-tetrachloroethane by reaction for hydration of trichloroethylene and/or 1,1,1,2-tetrachloroethane under pressure of hydrogen chloride in liquid phase, in the presence of ferric chloride in partial suspension.

16 Claims, No Drawings

PRODUCTION OF MONOCHLOROACETYL CHLORIDE AND MONOCHLOROACETIC ACID BY HYDRATION OF TRICHLOROETHYLENE

The present invention concerns a process for the production of monochloroacetyl chloride accompanied if need be by monochloroacetic acid, by hydration of trichloroethylene and/or 1,1,1,2-tetrachloroethane, in the presence of an iron chloride catalyst.

It is known for monochloroacetic acid to be prepared in accordance with U.S. Pat. No. 1,304,108 by the hydration reaction of trichloroethylene at a temperature of from 150° to 200° C., in the presence of sulphuric acid in a concentration of at least 95% or in the presence of oleum, as the hydration agent.

The patentees take as their basis the performance of hypothetical reactions, in order to explain the formation of monochloroacetic acid, such reactions being as follows:

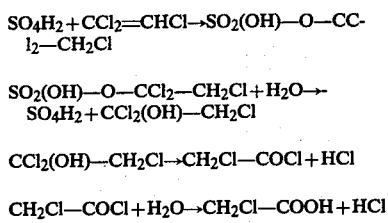

$$SO_4H_2 + CCl_2 = CHCl \rightarrow SO_2(OH) - O - CCl_2 - CH_2Cl$$

$$SO_2(OH) - O - CCl_2 - CH_2Cl + H_2O \rightarrow SO_4H_2 + CCl_2(OH) - CH_2Cl$$

$$CCl_2(OH) - CH_2Cl \rightarrow CH_2Cl - COCl + HCl$$

$$CH_2Cl - COCl + H_2O \rightarrow CH_2Cl - COOH + HCl$$

which, taken overall, makes it seem as if water alone produces the conversion effect:

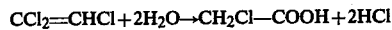

$$CCl_2 = CHCl + 2H_2O \rightarrow CH_2Cl - COOH + 2HCl$$

However, the intermediate formation of monochloroacetyl chloride has not been demonstrated or displayed, as is clearly apparent from French Pat. No. 516,367 which specifies production of monochloroacetic acid exclusively, by reacting water and trichloroethylene in the presence of 90% sulphuric acid at a temperature of 190° C.

Swiss Pat. No. 86,192 specifically describes the production of monochloroacetyl chloride from trichloroethylene, also by heating at about 110° C. with sulphuric acid but in the anhydrous state (100%). This process cannot therefore involve a trichloroethylene hydration reaction.

More recently, U.S. Pat. No. 3,742,047 described a process for producing monochloroacetyl chloride by reacting a mixture of trichloroethylene and monochloroacetic acid with a derivative of sulphonic acid or sulphuric acid at a temperature of from 75° to 125° C. The acid used in this reaction is essentially free from water, such as 100% sulphuric acid or toluenesulphonic, methanesulphonic, ethanesulphonic and chlorosulphonic acids. In the case of 100% sulphuric acid, the reaction may be written as follows:

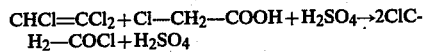

$$CHCl = CCl_2 + Cl - CH_2 - COOH + H_2SO_4 \rightarrow 2ClCH_2 - COCl + H_2SO_4$$

However, this process consumes monochloroacetic acid, while in itself it is a useful starting product for many synthesis operations, for example that of compounds which enjoy herbicidal properties or parasiticidal properties, containing the chloroacetyl group. In addition, performance of the reaction requires strict monitoring of the temperature which must not exceed 125° C. as, above that temperature, polymerization, sulphonation and dehydration (anhydrides) by-products are formed.

According to French Pat. No. 2,070,428, this last reaction can be performed under hydrogen chloride pressure, but using ferric chloride as the catalyst instead of sulphuric or sulphonic acid. However, like the above-mentioned process, this process also consumes monochloroacetic acid. In addition, for continuous operation of the process, it is necessary to introduce under pressure monochloroacetic acid in the molten state, and the anhydrous catalyst in solid form, while trichloroethylene is in liquid phase. These operations give rise to technical problems which are difficult to overcome.

The process disclosed in French Pat. No. 2,070,427, which differs from that of the preceding French patent only by the starting reagent which is 1,1,1,2-tetrachloroethane, instead of trichloroethylene, suffers from the same technical difficulties which impede easy performance of the process on an industrial scale.

The aim of the present invention is to overcome the abovementioned disadvantages by using a simple process for the continuous production of monochloroacetyl chloride, accompanied, if necessary, by monochloroacetic acid, by the direct action of water on trichloroethylene, in accordance with the following reaction:

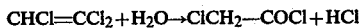

$$CHCl = CCl_2 + H_2O \rightarrow ClCH_2 - COCl + HCl$$

According to the invention, water is reacted with trichloroethylene and/or 1,1,1,2-tetrachloroethane, said hydration reaction being effected in liquid phase in the presence of ferric chloride, partially in suspension, and under hydrogen chloride pressure, at a temperature of from 80° to 180° C.

The hydrogen chloride pressure for carrying out the process of the invention is from 5 to 80 bars absolute pressure, more advantageously from 15 to 60 bars absolute pressure, and preferably from 20 to 40 bars absolute pressure.

It has been found that reaction speed reaches a maximum value at a specific temperature for a given pressure within the described range. This makes it possible to define a preferred temperature range which embraces that specific temperature for the selected operating pressure. For example, when operation is at a pressure of 30 bars absolute, it is observed that, at temperatures below 100° C. and at temperatures above 180° C., reaction is virtually negligible, and the speed of reaction begins to decrease from about 160° C., so that the preferred reaction temperature range is from 140° to 170° C.

According to the invention, the molar ratio between the feed reagents trichloroethylene and/or 1,1,1,2-tetrachloroethane and water is generally at least 0.6. It is found that the amount of monochloroacetic acid which accompanies the monochloroacetyl chloride increases as the molar ratio between the feed trichloroethylene and/or 1,1,1,2-tetrachloroethane and water approaches a value of 0.6. In contrast, when this molar ratio assumes values above 2, the amounts of undesirable secondary products such as pentachloroethane and perchloroethylene, resulting from the additive chlorination of trichloroethylene by $FeCl_3$ and the attendant reduction of a part of $FeCl_3$ to $FeCl_2$, and pentachlorobutadiene resulting from the dimerization of trichloroethylene become evident and even substantial, so that it is very possible to operate at molar ratios of from 2.5 to 3 for example, if such secondary products are desired.

In the event that it is desired to produce monochloroacetyl chloride with a very good degree of selectivity, it is desirable to use molar ratios of feed trichloroethylene and/or 1,1,1,2-tetrachloroethane to water of from 1.2 to 1.8.

When it is desired simultaneously to produce substantial amounts of monochloroacetyl chloride and monochloroacetic acid, the molar ratio between the feed trichloroethylene and/or 1,1,1,2-tetrachloroethane and water is selected at a value of from 0.6 to 1.2.

The amount of ferric chloride which is introduced into the reaction medium is from 0.1 to 15% by weight of the reaction medium except for the hydrogen chloride, both in gaseous form and that which is dissolved therein. Below a value of 0.1% by weight of $FeCl_3$, the reaction speed is excessively slow, whereas above 15% by weight, the separation and subsequent recovery of the catalyst in the reaction medium become complicated. When ferrous chloride is formed, in consequence of the undesired reactions set out above, the catalyst may be separated from the reaction medium by any known means and the ferrous chloride may be re-oxidized to $FeCl_3$ by gaseous chlorine or an agent capable of liberating the active chlorine such as chlorine water, Javel water, or chlorine dioxide or, generally, by any HCl oxidizing agent. The catalyst which is regenerated in this way can then be recycled to the reaction medium.

In accordance with a particularly advantageous embodiment of the process of the invention, the ferric chloride is introduced into the reaction medium in the form an an aqueous solution.

In a method of recovery of the catalyst, within the scope of the process of the invention, the effluent from the reaction zone is subjected to a fractionation to separate the unreacted chlorinated hydrocarbons and the monochloroacetyl chloride, from the mixture containing the ferrous and ferric chlorides. This mixture is treated with water and re-oxidized, for example, by chlorine, and the resulting ferric solution is then recycled to the reaction zone.

The residence time of the reactants in the reaction zone, calculated on the input flow rates, is generally from 1 to 8 hours and preferably from 2 to 6 hours.

According to the invention, the starting trichloroethylene may originate from 1,1,1,2-tetrachloroethane which, under the conditions of the hydration reaction of the invention, undergoes at least partial dehydrochlorination, in situ, to trichloroethylene, thus establishing an equilibrium, which depends on the temperature and pressure used, between 1,1,1,2-tetrachloroethane and trichloroethylene. So that it is possible for the starting product used according to the invention, to be trichloroethylene and/or 1,1,1,2-tetrachloroethane, which is expressed by the molar ratio between the reagents trichloroethylene and/or 1,1,1,2-tetrachloroethane and water.

Thus, within the scope of a continuous process, 1,1,1,2-tetrachloroethane, in the same way as monochloroacetic acid, is a useful by-product which may be recycled with the trichloroethylene of the feed. As for its part, the monochloroacetic acid which is possibly formed, may, if desired, advantageously be recycled in mixture with the ferric chloride, particularly when the latter is used in the form of an aqueous solution. In such instance, the amount of ferric chloride is greater than 20% by weight with respect to the quantity of monochloroacetic acid present in the reaction medium, and may exceed up to ten times the weight of that acid which is present.

The following examples are given by way of illustration and not by way of limitation of the present invention.

In these examples, the conversion rate of trichloroethylene and/or 1,1,1,2-tetrachloroethane used, according to circumstances, as the starting substance, is defined by the ratio:

$$\frac{\text{number of moles of } (CCl_2=CHCl + CCl_3CH_2Cl) \text{ converted}}{\text{number of moles of } (CCl_2=CHCl + CCl_3CH_2Cl) \text{ fed to the reactor}} \times 100$$

with the numerator equal to the difference between the number of moles of $(CCl_2=CHCl + CCl_3CH_2Cl)$ fed to the reactor, and the number of moles of $(CCl_2=CHCl + CCl_3CH_2Cl)$ exiting from the reactor.

The selectivity in respect of $ClCH_2—COCl$ is defined by the ratio:

$$\frac{\text{number of moles of } ClCH_2—COCl \text{ produced}}{\text{number of moles of } (CCl_2=CHCl + CCl_3CH_2Cl) \text{ converted}} \times 100$$

The selectivity in respect of $ClCH_2—COOH$ is defined by the following ratio:

$$\frac{\text{number of moles of } ClCH_2—COOH \text{ produced}}{\text{number of moles of } (CCl_2=CHCl + CCl_3—CHCl) \text{ converted}} \times 100$$

EXAMPLE 1

1264 kg/h (9.61 kmoles) of trichloroethylene and 181 kg/h of an aqueous solution of $FeCl_3$ containing 40.3% of $FeCl_3$ (0.45 kmole of $FeCl_3$ and 6 kmoles of $H_2O$) are continuously introduced into a glass-lined steel reaction vessel which is agitated and provided with pressure and level control means.

The molar ratio between the trichloroethylene and water is 1.6 and the amount of $FeCl_3$ represents 5.8% by weight of the reaction medium except for HCl (both in gaseous form and that which is dissolved therein).

The pressure in the reactor is maintained at 30 bars absolute pressure and the temperature is fixed at 150° C. The residence time of the reagents is 4 hours. From the reactor, there is continuously drawn 1257 kg/h of liquid apart from dissolved HCl containing:
656.5 kg of monochloroacetyl chloride
9.5 kg of monochloroacetic acid
366 kg of trichloroethylene
141 kg of 1,1,1,2-tetrachloroethane
16 kg of chlorinated heavy substances (boiling point >150° C.)
49 kg of $FeCl_3$
19 kg of $FeCl_2$ A total of 5.16 kmoles/h of HCl is recovered, corresponding to the HCl drawn off continuously in the gaseous phase and to the dissolved HCl evolved by subsequent pressure release of the liquid effluent.

In order to recover the catalyst, this effluent is fractionated to separate the monochloroacetyl chloride and the unreacted chlorinated hydrocarbons, from the mixture containing the ferrous and ferric chlorides. This mixture is treated with water and re-oxidized by chlorine to give a ferric solution before being recycled to the reactor.

The conversion rate, the degrees of selectivity in respect of ClCH₂—COCl and ClCH₂—COOH as defined above are respectively 62.3%, 97.0% and 1.7%.

EXAMPLE 2

Following the same stages of the process and under the same temperature and hydrogen chloride pressure conditions as set out in Example 1, 1151 kg/h (8.75 kmoles) of trichloroethylene and 266.5 kg/h of an aqueous solution of $FeCl_3$ containing 27.3% by weight of $FeCl_3$ (10.75 kmoles of $H_2O$ and 0.45 kmoles/m³ of $FeCl_3$) is continuously introduced into the reactor.

The trichloroethylene/water molar ratio is 0.81. The amount of $FeCl^3$ represents 7.1% by weight of the reaction medium except for HCl (both that dissolved and that in gaseous form).

The intake flow rate of the reagents is 1 m³/h. The residence time of the reagents in the reactor is 4 hours. 1032 kg/h of the following reaction product, apart from dissolved HCl, is drawn off from the reactor:
430.5 kg of monochloroacetyl chloride
328 kg of monochloroacetic acid
167 kg of trichloroethylene
32 kg of 1,1,1,2-tetrachloroethane
2 kg of chlorinated heavy products (boiling point >150° C.).
70 kg of $FeCl_3$
2.6 kg of $FeCl_2$
10.56 kmoles/h of HCl recovered.

The conversion rate, the degrees of selectivity of $CH_2Cl$—COCl and $CH_2Cl$—COOH as defined above are respectively 83.3%, 52.3% and 47.6%.

EXAMPLE 3

Following the same steps of the process and under the same temperature, residence time and hydrogen chloride pressure conditions as set out in Example 1, the following are continuously introduced into the reactor:
1249.5 kg/h (9.5 kmoles) of trichloroethylene
190.5 kg/h (7.6 kmoles $H_2O$ and 0.33 kmoles $FeCl_3$) of aqueous solution of $FeCl_3$ containing 28.1% by weight of $FeCl_3$.

The trichloroethylene/water molar ratio is 1.25. The amount of $FeCl_3$ represents 4.5% by weight of the reaction mixture except for the hydrogen chloride which is dissolved therein, and also that which is in the gaseous state.

The intake flow rate of the reactants is 1 m³/h.
1188.5 kg/h of the following reaction product, apart from dissolved HCl, is drawn from the reactor:
447 kg of monochloroacetyl chloride
172 kg of monochloroacetic acid
393 kg of trichloroethylene
119 kg of 1,1,1,2-tetrachloroethane
6 kg of chlorinated heavy products (boiling point >150° C.)
45.5 kg of $FeCl_3$
6 kg of $FeCl_2$
6.89 kmoles/h of HCl recovered.

The conversion rate, the degrees of selectivity in respect of $CH_2Cl$—COCl and $CH_2$ Cl—COOH as defined above are respectively 61.1%, 68.3% and 31.4%.

EXAMPLE 4

Carrying out the same steps of the process and under the same temperature and HCl pressure conditions as set out in Example 1, the following are continuously introduced into the reactor:
1663.5 kg/h (12.65 kmoles) of trichloroethylene
260.5 kg/h (9.05 kmoles $H_2O$ and 0.6 kmole $FeCl_3$) of aqueous solution containing 37.4% by weight of $FeCl_3$.

The trichloroethylene/water molar ratio is 1.4. The intake flow rate of the reagents is 1.33 m³/h. The residence time of the reagents in the reactor is 3 hours. The amount of $FeCl_3$ represents 5.9% by weight with respect to the reaction medium apart from HCl (both that in the gaseous state and that in the dissolved state).

1649 kg/h of reaction product apart from dissolved HCl is then drawn from the reactor:
545 kg of monochloroacetyl chloride
200 kg of monochloroacetic acid
539 kg of trichloroethylene
254 kg of 1,1,1,2-tetrachloroethane
24 kg of chlorinated heavy products (boiling point >150° C.)
57 kg of $FeCl_3$
30 kg of $FeCl_2$
7.54 kmoles/h of HCl recovered.

The conversion rate, the degrees of selectivity in respect of $CH_2Cl$—COCl and $CH_2Cl$—COOH as defined above are respectively 55.7%, 68.5% and 30.1%.

EXAMPLE 5

Under the same temperature and HCl pressure conditions and performing the same steps in the process as set out in Example 1, the following are continuously introduced into the reactor:
1097 kg of trichloroethylene
196 kg/h of recycled 1,1,1,2-tetrachloroethane resulting from the effluent of the reactor
110 kg/h of water
90 kg/h of recycled monochloroacetic acid also resulting from the effluent of the reactor
66 kg/h of $FeCl_3$ of which 95% comes from recycling of the catalyst recovered from the effluent of the reactor The molar ratio between $(CHCl=CCl_2+CCl_3-CH_2Cl)$ and $H_2O$ is 1.56. The intake flow rate into the reactor of the components of the reaction mixture is about 1 m³/h, and the residence time of the components in the reactor is four hours. The amount of $FeCl_3$ represents 4.9% by weight of the reaction medium HCl excepted (both that in the dissolved state and that in the gaseous state).

1336 kg/h of the following reaction mixture, except for dissolved HCl, is drawn from the reactor:
690.5 kg of monochloroacetyl chloride
90 kg of monochloroacetic acid
284 kg of trichloroethylene
196 kg of 1,1,1,2-tetrachloroethane
14.5 kg of chlorinated heavy products (boiling point >150° C.)
45 kg of $FeCl_3$
16 kg of $FeCl_2$
6.11 kmoles/h of HCl recovered The conversion rate of the feed trichloroethylene and 1,1,1,2-tetrachloroethane, and the selectivity in respect of ClCH$_2$—COCl as defined above are respectively 65% and 98.9%.

EXAMPLE 6

Under the same temperature and HCl pressure conditions and carrying out the same operations as set out in Example 1, the following are continuously introduced into the reactor;
2125 kg/h of 1,1,1,2-tetrachloroethane
260.5 kg/h (9.05 kmoles H$_2$O and 0.6 kmole FeCl$_3$) of aqueous solution containing 37.4% by weight of FeCl$_3$.

The 1,1,1,2-tetrachloroethane/water molar ratio is 1.4 and the intake flow rate of the reagents is 1.49 m$^3$/h.

The residence time of the reagents in the reactor is 2.7 hours. The amount of FeCl$_3$ represents 6% by weight with respect to the reaction medium except for HCl (both that in the dissolved states and that in the gaseous state).

1632.5 kg/h of the following reaction product, except for dissolved HCl, is then drawn from the reactor:
864.5 kg of monochloroacetyl chloride
65 kg of monochloroacetic acid
393 kg of trichloroethylene
201.5 kg of 1,1,1,2-tetrachloroethane
18 kg of chlorinated heavy products (boiling point >150° C.)
25.5 kg of FeCl$_2$
65 kg of FeCl$_3$
20.6 kmoles/h of HCl recovered The conversion rate of 1,1,1,2-tetrachloroethane and the degrees of selectivity in respect of CH$_2$Cl—COCl and CH$_2$Cl—COOH are respectively 66.9%, 90.4% and 8.2%.

We claim:

1. A continuous process for the production of monochloroacetyl chloride, which may be accompanied by monochloroacetic acid, from trichloroethylene and/or 1,1,1,2-tetrachloroethane, comprising hydrating trichloroethylene and/or 1,1,1,2-tetrachloroethane under pressure of hydrogen chloride in liquid phase in the presence of ferric chloride partially in suspension, in which the hydrogen chloride pressure is within the range of 5-80 bars absolute.

2. A process as claimed in claim 1 characterized in that hydration is effected at a temperature of from 80° to 180° C.

3. A process as claimed in claim 1 characterized in that hydration is effected at a temperature of from 140° to 170° C.

4. A process as claimed in claim 1 in which the ferric chloride is introduced into the reaction medium in the form of an aqueous solution.

5. A process as claimed in claim 1 in which the trichloroethylene and/or 1,1,1,2-tetrachloroethane and water are introduced into the reaction zone in a molar ratio greater than 0.6.

6. A process as claimed in claim 1 in which the trichloroethylene and/or 1,1,1,2-tetrachloroethane and water are in a molar ratio of from 1.2 to 1.8.

7. A process as claimed in claim 1 in which the trichloroethylene for the feed originates at least partially from the in situ dehydrochlorination of 1,1,1,2-tetrachloroethane.

8. A process as claimed in claim 1 in which the trichloroethylene for the feed originates from the in situ dehydrochlorination of 1,1,1,2-tetrachloroethane.

9. A process as claimed in claim 1 in which any monochloroacetic acid which is formed is recycled to the reaction medium.

10. A process as claimed in claim 1 in which the amount of FeCl$_3$ is from 0.1 to 15% by weight of the whole of the reaction medium, except for the hydrogen chloride both in the gaseous state and that which is dissolved therein.

11. A process as claimed in claim 1 in which monochloroacetic acid is formed and is recycled in mixture with the ferric chloride solution.

12. A process as claimed in claim 11 in which the amount of ferric chloride is higher than 20% by weight with respect to the amount of monochloroacetic acid present in the reaction medium.

13. A process as claimed in claim 1 in which the hydrogen chloride pressure is from 5 to 80 bars absolute.

14. A process as claimed in claim 1 in which the hydrogen chloride pressure is from 20 to 40 bars absolute.

15. A process as claimed in claim 1 in which, in the case where the ferric chloride of the reaction medium gives ferrous chloride as a consequence of secondary reactions, the ferrous chloride is re-oxidized by active chlorine to FeCl$_3$.

16. A process as claimed in claim 12 comprising fractionating the reaction medium effluent to separate the unreacted chlorinated hydrocarbons and monochloroacetyl chloride from the mixture containing the ferrous and ferric chlorides before reoxidation of the ferrous chloride.

* * * * *